(12) United States Patent
Di Achille et al.

(10) Patent No.: US 11,246,496 B2
(45) Date of Patent: Feb. 15, 2022

(54) HEART RATE AND BLOOD PRESSURE MONITORING BIOSENSORS

(71) Applicant: INTERNATIONAL BUSINESS MACHINES CORPORATION, Armonk, NY (US)

(72) Inventors: Paolo Di Achille, White Plains, NY (US); Viatcheslav Gurev, Yorktown Heights, NY (US); John J. Rice, Mohegan Lake, NY (US); Katsuyuki Sakuma, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 340 days.

(21) Appl. No.: 15/901,375

(22) Filed: Feb. 21, 2018

(65) Prior Publication Data

US 2019/0254541 A1 Aug. 22, 2019

(51) Int. Cl.
*A61B 5/021* (2006.01)
*A61B 5/024* (2006.01)
*A61B 5/00* (2006.01)

(52) U.S. Cl.
CPC ...... *A61B 5/02125* (2013.01); *A61B 5/02416* (2013.01); *A61B 5/6813* (2013.01); *A61B 5/6831* (2013.01)

(58) Field of Classification Search
None
See application file for complete search history.

(56) References Cited

U.S. PATENT DOCUMENTS

| 3,956,927 | A | * | 5/1976 | Pearson | G01L 1/2281 |
| | | | | | 73/766 |
| 4,331,154 | A | * | 5/1982 | Broadwater | A61B 5/021 |
| | | | | | 600/490 |
| 4,676,253 | A | | 6/1987 | Newman et al. | |
| 5,241,964 | A | * | 9/1993 | McQuilkin | A61B 5/02125 |
| | | | | | 600/485 |

(Continued)

OTHER PUBLICATIONS

C-C. Tyan et al., "A novel noninvasive measurement technique for analyzing the pressure pulse waveform of the radial artery," IEEE Transactions on Biomedical Engineering, vol. 55, No. 1, 2008, pp. 288-297.

(Continued)

*Primary Examiner* — Michael R Bloch
(74) *Attorney, Agent, or Firm* — Cantor Colburn LLP; Kristofer Haggerty

(57) ABSTRACT

Embodiments of the present invention are directed to a systems and methods for registration of pulse wave signal and determining arterial pressure. A non-limiting example of the system includes a strain gauge sensor. A non-limiting example of the method includes receiving, to a processor, a first pressure pulse signal from a first strain gauge sensor. The method also includes receiving, to the processor, a second pressure pulse signal from a second strain gauge sensor. The method also includes determining a pulse transit time between the first strain gauge sensor and the second strain gauge sensor based at least in part upon the first pressure pulse signal and the second pressure pulse signal. The method also includes determining an arterial pressure based at least in part upon the pulse transit time.

6 Claims, 20 Drawing Sheets

(56) References Cited

U.S. PATENT DOCUMENTS

| | | | | |
|---|---|---|---|---|
| 5,704,363 | A * | 1/1998 | Amano | A61B 5/021 |
| | | | | 600/500 |
| 6,443,906 | B1 * | 9/2002 | Ting | A61B 5/022 |
| | | | | 600/490 |
| 6,511,436 | B1 * | 1/2003 | Asmar | A61B 5/021 |
| | | | | 600/481 |
| 7,374,542 | B2 | 5/2008 | Kuchler | |
| 8,628,477 | B2 | 1/2014 | Addison et al. | |
| 9,162,065 | B2 | 10/2015 | Karst et al. | |
| 9,706,964 | B2 | 7/2017 | Ferber et al. | |
| 2003/0135097 | A1 * | 7/2003 | Wiederhold | A61B 5/02055 |
| | | | | 600/301 |
| 2006/0217616 | A1 | 9/2006 | Kuchler | |
| 2008/0039731 | A1 * | 2/2008 | McCombie | A61B 5/02255 |
| | | | | 600/485 |
| 2008/0071151 | A1 * | 3/2008 | Sogin | C12Q 1/485 |
| | | | | 600/301 |
| 2010/0268093 | A1 * | 10/2010 | Balji | A61B 5/04087 |
| | | | | 600/484 |
| 2011/0208071 | A1 * | 8/2011 | Lu | A61B 5/02125 |
| | | | | 600/500 |
| 2013/0144176 | A1 * | 6/2013 | Lee | A61B 5/021 |
| | | | | 600/485 |
| 2014/0043457 | A1 * | 2/2014 | Stergiou | A61B 5/6898 |
| | | | | 348/77 |
| 2016/0278651 | A1 | 9/2016 | Lu et al. | |
| 2017/0231490 | A1 * | 8/2017 | Toth | A61B 5/1075 |
| | | | | 600/558 |
| 2017/0367654 | A1 * | 12/2017 | Cheng | A61B 5/103 |
| 2020/0060558 | A1 * | 2/2020 | Aleksov | A61B 5/02141 |

OTHER PUBLICATIONS

A. Patzak et al., "Continuous blood pressure measurement using the pulse transit time: comparison to intra-arterial measurement," Blood Pressure, vol. 24, No. 4, 2015, pp. 217-221.

Devin B. McCombie et al., "Adaptive blood pressure estimation from wearable PPG sensors using peripheral artery pulse wave velocity measurements and multi-channel blind identification of local arterial dynamics", 28th Annual Int'l Conf., NYC, Aug. 30-Sep. 3, 2006; 4 pages.

H. Gesche et al., "Continuous blood pressure measurement by using the pulse transit time: comparison to a cuff-based method," European Journal of Applied Physiology, vol. 112, No. 1, 2012, pp. 309-315.

S. Puke et al., "Blood pressure estimation from pulse wave velocity measured on the chest," 35th Annual International Conference of the IEEE Engineering in Medicine and Biology Society, 2013, pp. 6107-6110.

\* cited by examiner

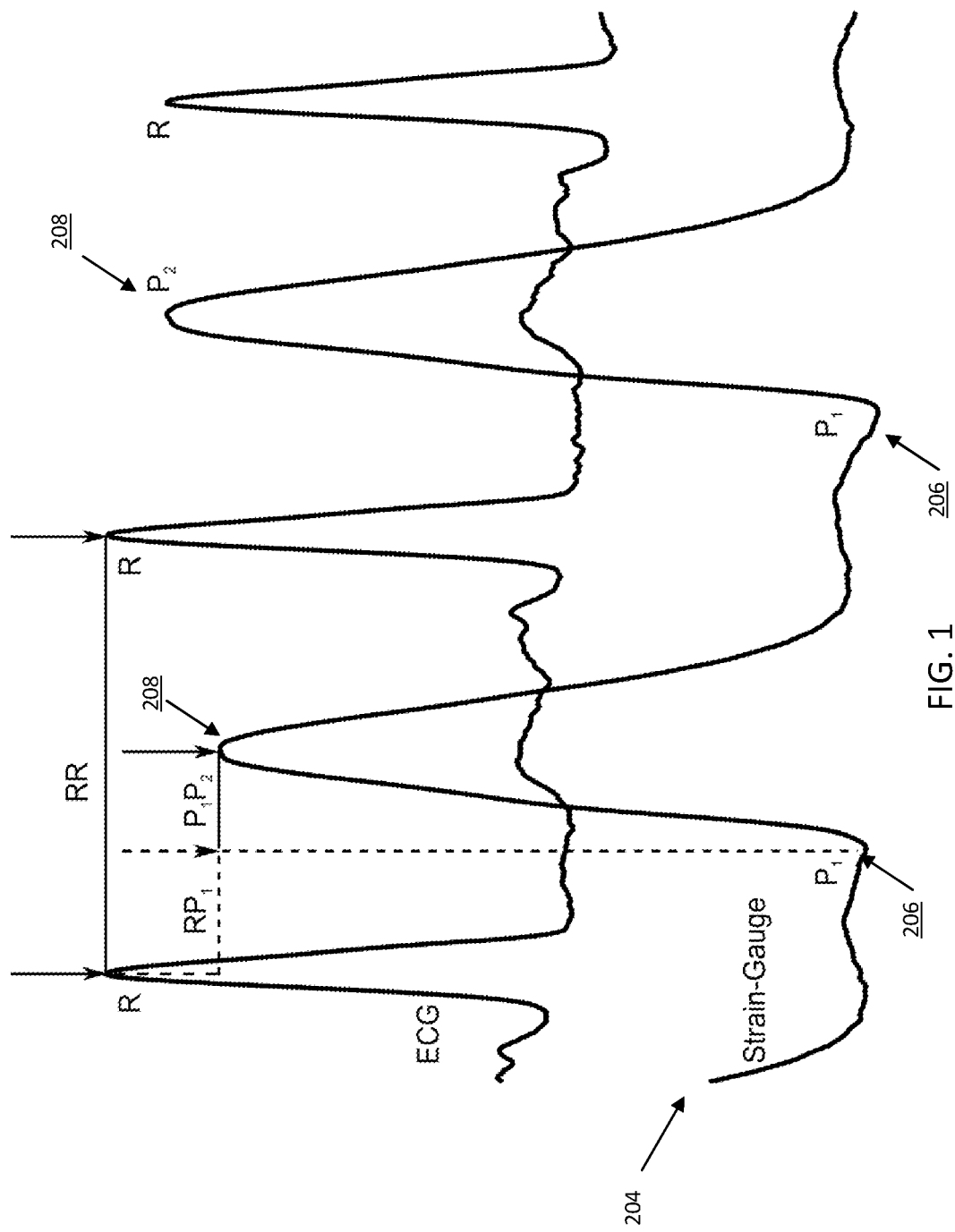

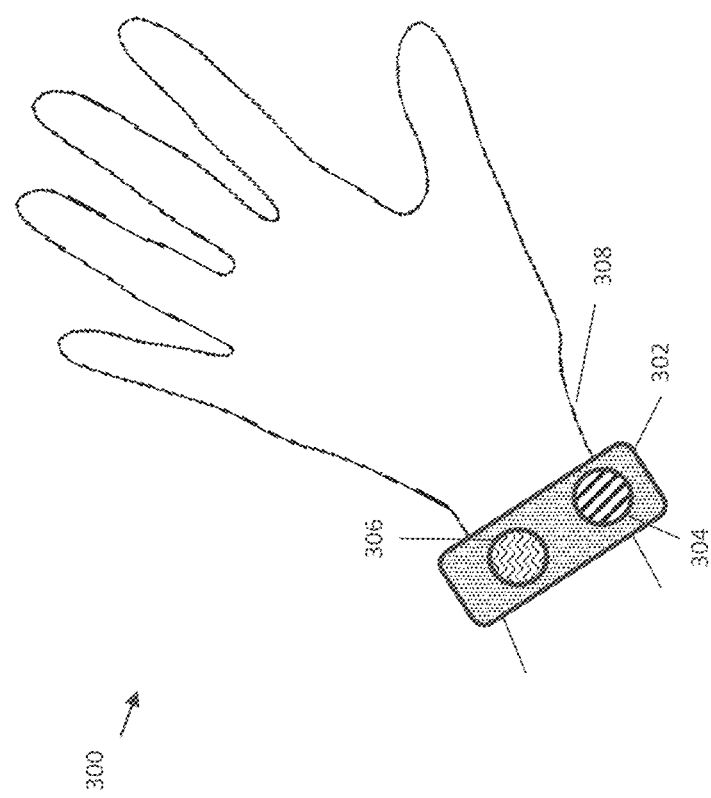

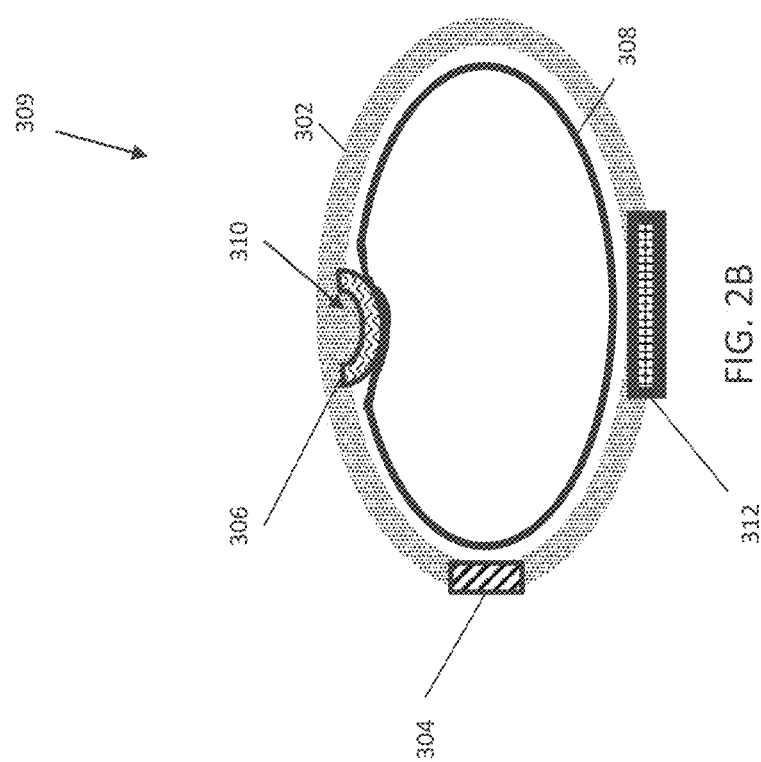

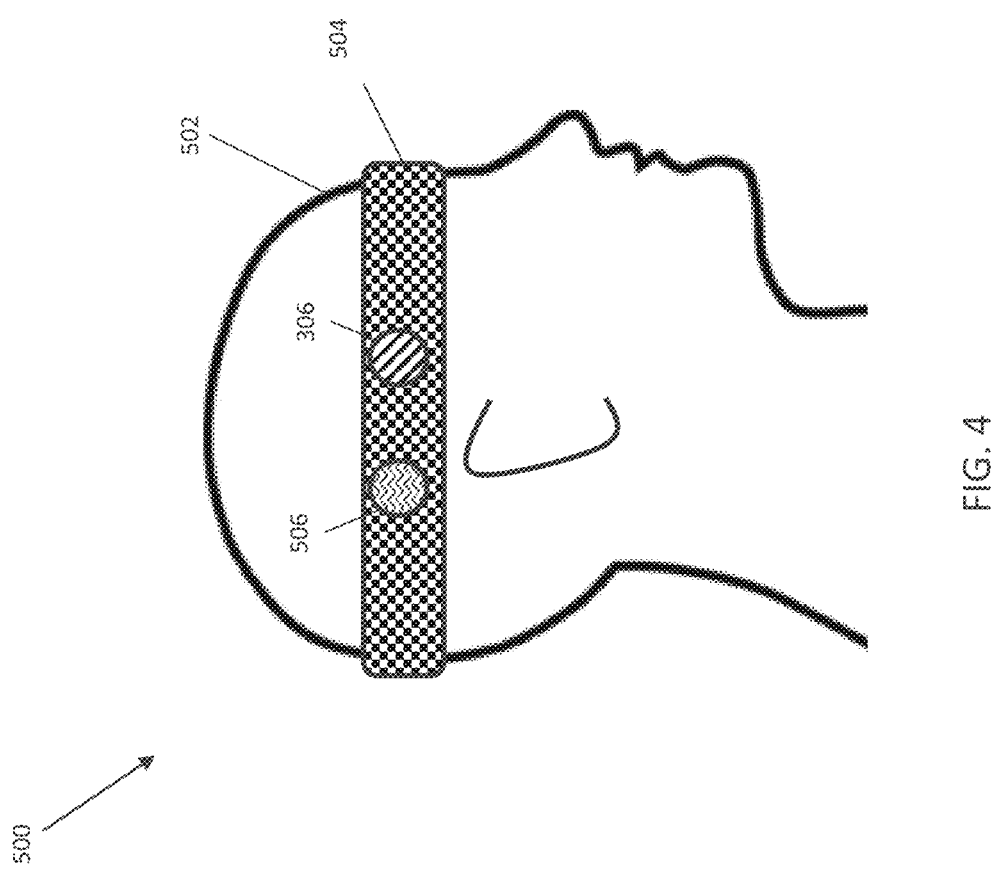

HEART RATE AND BLOOD PRESSURE MONITORING BIOSENSORS

BACKGROUND

The present invention generally relates to fabrication methods and resulting structures for biosensors. More specifically, the present invention relates to heart rate and blood pressure monitoring using wearable sensors.

Blood pressure and pulse monitoring can be important in the treatment and prevention of a variety of medical conditions. For example, monitoring pressure pulse waves, heart rate variability, and arterial pressure can be important to characterize cardiovascular disease and other conditions involving altered cardiac function. Heart contractions generate pulse waves that travel to peripheral arteries. The characteristics of such pulse waves can provide a number of insights into the status of internal systems. For example, the speed of travel of the pulse waves and rhythmically of pulse waves can correlate to arterial stiffness, heart rate variability, and blood pressure. Monitoring and characterizing aspects of blood flow, such as pressure pulse wave characteristics and arterial pressure, can provide indicators, for instance, of cardiovascular events, hypertension, organ damage, and even lung function.

SUMMARY

Embodiments of the present invention are directed to a computer implemented method for determining arterial pressure. A non-limiting example of the method includes receiving, to a processor, a first pressure pulse signal from a first strain gauge sensor. The method also includes receiving, to the processor, a second pressure pulse signal from a second strain gauge sensor. The method also includes determining a pulse transit time between the first strain gauge sensor and the second strain gauge sensor based at least in part upon the first pressure pulse signal and the second pressure pulse signal.

Embodiments of the present invention are directed to a computer-implemented method for determining arterial pressure. A non-limiting example of the method includes receiving, to a processor, an electrocardiogram (ECG) signal from an ECG electrode. The method also includes receiving, to the processor, a pressure pulse waveform from a strain gauge sensor. The method also includes extracting, by the processor, an ECG feature from the ECG signal. The method also includes extracting, by the processor, a pressure pulse wave feature from the pressure pulse waveform. The method also includes determining, by the processor, an arterial pressure based at least in part upon the pressure pulse wave features and the ECG features.

Embodiments of the present invention are directed to a biosensor system. A non-limiting example of the system includes a wearable sensor capable of detecting a pressure pulse wave signal through the skin of a subject. The system also includes a wearable device for affixing the wearable sensor to a skin of a subject. The system also includes a circuitry module including a control unit for receiving signals from the wearable sensor and a data communication unit capable of communicating with an external device.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 1 depicts representative ECG and pulse wave signals from a strain-gauge sensor from an exemplary embodiment of the invention;

FIGS. 2A and 2B depict schematics of an exemplary biological monitoring system according to embodiments of the invention, in which FIG. 2A depicts a side view of the monitoring system positioned on a user and FIG. 2B depicts a top down view of the monitoring system positioned on the user;

FIGS. 3A and 3B depict schematics of an exemplary biological monitoring system according to embodiments of the invention, in which FIG. 3A depicts a side view of the monitoring system positioned on a user and FIG. 3B depicts a top down view of the monitoring system positioned on the user;

FIG. 4 depicts a schematic of another exemplary sensing system according to embodiments of the invention;

FIGS. 5A-5D depict schematics of an exemplary schematic of aspects of a piezoresistive-based strain gauge element according to embodiments of the invention, in which:

FIG. 5A depicts an exemplary schematic of aspects of a piezoresistive-based strain gauge element;

FIG. 5B depicts another exemplary schematic of aspects of a piezoresistive-based strain gauge element;

FIG. 5C depicts another exemplary schematic of aspects of a piezoresistive-based strain gauge element; and FIG. 5D depicts another exemplary schematic of aspects of a piezoresistive-based strain gauge element;

FIG. 16A-C show representative results from an exemplary embodiment of the invention with ECG and strain gauge sensors, in which:

FIG. 16A depicts data obtained with an exemplary system according to embodiments of the invention;

FIG. 16B depicts data obtained with an exemplary system according to embodiments of the invention; and FIG. 16C depicts computed systolic blood pressure obtained with an exemplary system according to embodiments of the invention.

Figure 3A:
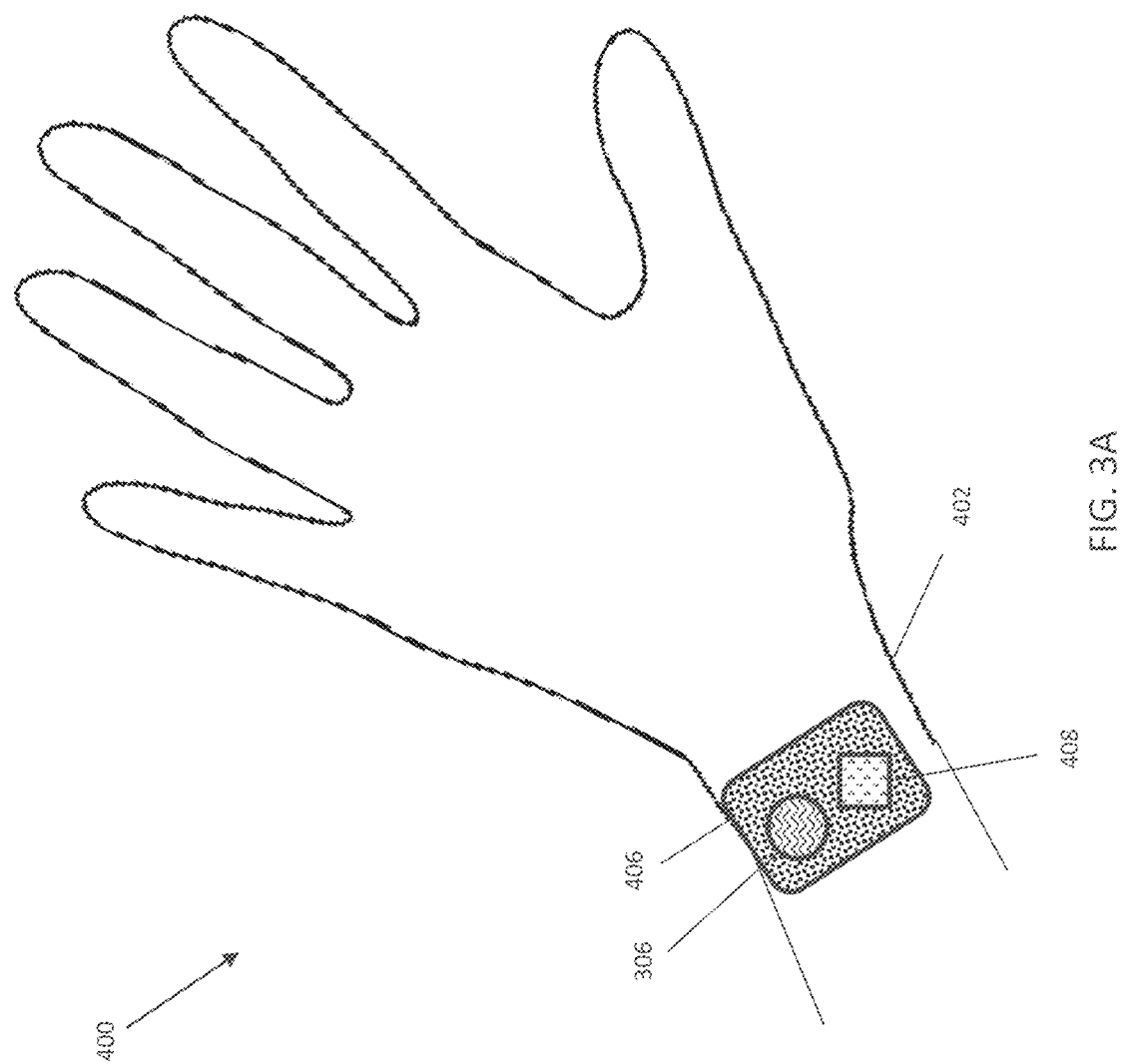

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three-digit reference numbers. With minor exceptions, the leftmost digit(s) of each reference number correspond to the figure in which its element is first illustrated.

DETAILED DESCRIPTION

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to an overview of technologies that are more specifically relevant to aspects of the invention, monitoring of pressure pulse waves, heart rate variability, and arterial pressure are important to prevent, treat, or manage cardiovascular diseases and ischemic strokes and other medical conditions.

A common conventional method to record pulse pressure waves is photoplethysmography. In photoplethysmography, blood volume changes in peripheral arteries are detected by optical sensors based on principles of light scattering. Such optical sensors can be placed on the chest, wrist, or finger of a subject.

Conventionally, non-invasive arterial pressure measurements can be measured by the sphygmomanometer, which includes inflatable cuffs commonly used in doctor's offices, clinics, and in home-based settings.

Conventional methods of measuring pressure pulse waves and arterial pressure suffer from a number of drawbacks. For example, photoplethysmography signals can be extremely sensitive to motion and, as such, are not useful for monitoring pressure pulse waves when a person walks or exercises. Sphygmomanometers and other known systems for measuring arterial pressure have a number of limitations. For instance, the sphygmomanometer, the most reliable device to measure arterial pressure (Pa), does not provide continuous measurements. Other methods can suffer from poor reliability issues.

Turning now to an overview of the aspects of the invention, one or more embodiments of the invention address the above-described shortcomings of the prior art by providing continuous estimation of heart rate variability and/or systolic and diastolic arterial pressure. Some embodiments of the invention provide non-invasive recording of pressure pulse waves at peripheral locations to determine heart rate variability and blood pressure. Some embodiments of the invention enable acquisition of heart and blood pressure data while a subject is in motion.

The above-described aspects of the invention address the shortcomings of the prior art by including semiconductor strain gauge materials to record transit time and wave form of the blood pressure wave. In some embodiments of the invention, semiconductor strain gauge sensors are included in patch systems that can be applied to the skin of a subject. In some embodiments of the invention, semiconductor strain gauge sensors are included in electrodes. Semiconductor strain gauge materials can be used to measure transit time and wave form of a blood pressure wave by placing sensors including semiconductor strain gauge materials on or near blood vessels, such as externally near an artery, such as on the neck, wrist, or temple, internally on or near an artery, or combinations of such placements. Sensors including semiconductor strain gauge materials can be used to determine blood pressure.

Embodiments of the invention can provide reliable, non-invasive measurements of vessel expansions induced by pressure pulse waves to provide blood pressure monitoring and subject health. The time interval needed by a pulse wave to travel from the heart to a peripheral artery or from a proximal artery to a distal one, referred to as pulse transit time (PTT), can provide information pertinent to monitoring subject health. Pressure pulse waves are generated as heart contractions cause blood to travel to peripheral arteries. A pulse pressure wave contains information relevant to a number of internal systems and processes. Pulse wave velocity depends, in part, on arterial pressure.

Systolic and diastolic arterial pressure can be estimated from PTT. PTT can be obtained by using two sensors that record electrocardiogram (ECG) and a plethysmogram, or two plethysmograms taken at different locations by either piezoelectric or piezoresistive sensors. Arterial pressure can be determined from PTT through the Moens-Korteweg equation, taking into account constitutive laws for arterial stiffness. Arterial pressure can, in some cases, be related to PTT by linear regression or non-linear formulas fit to experimental distributions of PTT-Pa data. Embodiments of the invention can measure blood flow characteristics through placement of strain gauge sensors using, for instance, Moens-Korteweg equation.

Turning now to a more detailed description of aspects of the present invention, FIG. 1 depicts exemplary pressure pulse wave charts. The chart depicts a typical ECG waveform 202. Methods and apparatuses for obtaining such signals are known. ECG signals can be, for example, digitized and analyzed according to various known methods to characterize a number of systemic features and conditions, such as heart rate and arrhythmias. The chart also depicts a strain gauge based wave form 204 that can be obtained according to embodiments of the invention. As shown, R represents an R peak, which can play an important role, for instance, in diagnosing heart rhythm abnormalities. According to embodiments of the invention, PTT can be obtained by using two sensors that record ECG and a plethysmogram. PTT is defined here as the time interval between the R-peak of the ECG, as shown, and the arrival of the pulse wave to one of the peripheral arteries (such as a radial artery), which can be observed via a strain gauge sensor according to embodiments of the invention as illustrated as point P1 206 in FIG. 1.

Systems according to embodiments of the invention can record pressure pulse waves at multiple peripheral locations, such as two or more locations, to characterize biological systems and conditions, including for instance characterization and determination of heart rate variability and systolic blood pressure. Sensors according to embodiments of the invention, including semiconductor or metal strain gauge sensors that use piezoresistive effect and/or piezoelectric-based strain gauge sensors and electrodes, can be used to record pulse transit time and the wave form of a blood pressure wave. Features of blood pressure wave form and ECG can be used, in some embodiments of the invention, for continuous estimation of systolic and diastolic arterial pressure.

Embodiments of the invention include sensors positioned on or near an artery. In some embodiments of the invention, biosensors, including strain gauge sensors, are placed on the skin at a location where an artery is capable of being compressed near the surface of the body, including at the carotid artery, brachial artery, radial artery, femoral artery, popliteal artery, posterior tibial artery, and/or the dorsalis pedis artery. In some embodiments of the invention, biosensors, including piezoresistive type strain gauge sensors and/or piezoelectric type strain gauge sensors, are implanted near an artery. For instance, biosensors can be inserted subcutaneously or can be placed directly on an artery. In some embodiments of the invention, biosensors are coated with a biocompatible material prior to insertion or implantation.

FIG. 2A depicts a side view of an exemplary biological monitoring system 300 according to embodiments of the invention. As is shown, aspects of a sensing system 300 can be applied to the surface of the skin at an area in close proximity to an artery, such the surface of the skin 308 at a wrist. The system 300 can include a piezoelectric or piezoresistive sensor unit 306 and a circuitry module 304. The piezoelectric or piezoresistive sensor unit can be a wearable sensor capable of detecting a pressure pulse wave through the skin of a subject. The circuitry module 304 can include, for example, a microcontroller, an amplifier, an analog to digital (A/D) converter, and a power and/or data communication unit capable of communicating wirelessly or via a wired connection to an external device such as smart phone, watch, tablet, notebook, etc. In some embodiments of the invention, the piezoelectric or piezoresistive sensor unit 306 and the circuitry module 304 are fastened to a band or belt 302 capable of encircling a body part, such as a wrist. The piezoelectric or piezoresistive sensor unit 306 is positioned, in some embodiments of the invention, against the surface of the skin. The circuitry module 304 can include a power source and can receive signals from the strain gauge sensor 306 and the external device, such as smart phone, watch, tablet, computer, or other electronic device.

FIG. 2B depicts a top down view of another exemplary biological monitoring system 309. The system 309 includes a piezoelectric or piezoresistive sensor unit 306, a circuitry module 304 electrically connected to the sensor unit 306, and a band or belt 302. The band or belt 302, as shown, includes a protrusion 310 at the location of the sensor unit 306 to improve or enhance contact between the sensor unit 306 and the surface of the skin 308. In some embodiments of the invention, the band or belt 302 includes a clasp 312 to fasten the band or belt 302 around the body.

Piezoelectric or piezoresistive sensor unit 306 can include piezoresistive based strain gauge sensors or piezoelectric based strain gauge sensors. In some embodiments of the invention, systems include biosensors including piezoelectric materials. In some embodiments of the invention, systems include semiconductor based strain guage sensors and piezoelectric based strain gauge sensors. As will be appreciated by those skilled in the art, the electrical properties of a semiconductor material in a semiconductor based strain gauge can be adjusted by modifying dopants and/or doping conditions, such as patterns and concentrations of dopant, depending on the desired properties and applications.

Embodiments of the invention include sensors including semiconductor and/or metal (e.g. nanoparticle based) strain gauge materials. Strain gauges measure strain that can be imparted by stress, torque, and a host of other stimuli such as displacement, acceleration, and position. The gauge factor for semiconductors can be several magnitudes larger than the gauge factor for metal. Thus, the change in conductivity due to strain can be much larger in semiconductor strain gauge materials relative to conductive strain gauge materials, providing highly sensitive strain detection and measurements.

Embodiments of the invention include metal based strain gauge sensors including, for example, nanoparticle-based materials, carbon nanotube based materials, nanofiber based materials, and/or combinations thereof.

In a semiconductor strain gauge material, a semiconductor substrate can provide a means of straining a silicon chip. Semiconductor base materials can be doped, for example by diffusion of doping materials, to obtain a desired base resistance. Advantageously, strain gauge materials can be several magnitudes smaller than metal sensors due in part on the difference in gauge factor. Strain gauges can be described, in some instances, with a function as follows:

$$\frac{\Delta R}{R} = \frac{\Delta \rho}{\rho} + \frac{\Delta L}{L} - \frac{\Delta A}{A}$$

where ρ is the resistivity of the material, L is the length of the material, A is the cross-sectional area of the material.

Methods of manufacturing strain gauge sensors, including semiconductor strain gauge sensors, are known. In some embodiments of the invention, a semiconductor base material of a semiconductor based strain gauge sensor can be doped. Doping can be selective doping, such that a specific area or region of the substrate is doped, or doping can be non-selective, for example such that the entire silicon substrate is doped to obtain a base resistance as needed. Non-limiting examples of suitable dopant materials include p-type dopants (e.g., boron), n-type dopants (e.g., phosphorus, arsenide, antimony), or any combination thereof. A substrate can provide strain for a silicon chip. In some embodiments, metal connections can be provided at the ends of a device.

Piezoelectric materials that can be used include, for instance, perovskite based materials and non-perovskite piezo-electric materials. Piezoelectric materials can include, for example, lead zirconate titanates (PZTs), potassium niobate, sodium tungstate, barium titanate (BaTiO$_3$), and lead titanate (PbTiO$_3$). Piezoelectric materials that directly generate a voltage that is a function of the strain can advantageously have higher efficiency than piezoresistive materials and can require less surface area. Moreover, piezoelectric based strain gauge sensors can be integrated in back end of the line (BEOL) of semiconductor manufacturing process.

Selected exemplary properties of piezoelectric materials and piezoresistive materials (semiconductor based strain gauge materials) are depicted below. The properties of piezoelectric materials can be varied, for instance depending on materials used, based upon the desired properties and applications.

| Material | Strain sensitivity (V/µε) | Threshold (µε) | Span to threshold ratio |
|---|---|---|---|
| Piezoelectric | 5.0 | 0.00001 | 100,000,000 |
| Piezoresistive | 0.0001 | 0.0001 | 2,500,000 |

Figure 3B:
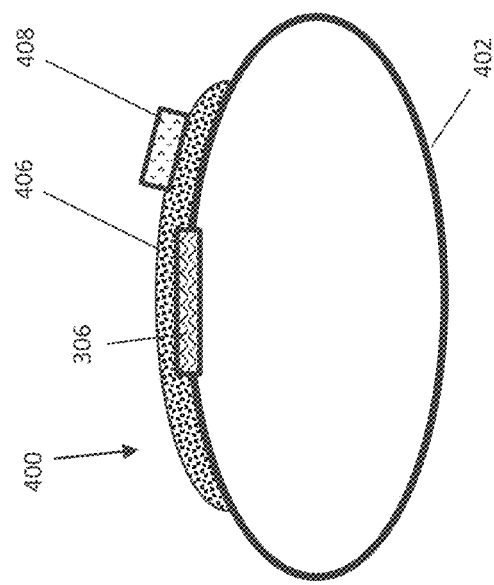

FIGS. 3A and 3B depict another exemplary system 400 according to one or more embodiments of the invention, in which FIG. 3A depicts a side view of a system 400 according to an exemplary embodiment of the invention applied to the surface of the skin at an area in close proximity to an artery, such the surface of the skin at a wrist 402. FIG. 3B shows a top down view of the system 400. The system 400 can include a piezoelectric or piezoresistive sensor unit 306, an adhesive patch 406, and a circuitry module 408, including control and communication circuitry for the strain gauge sensor. The strain gauge sensor can include a piezoresistive material (e.g. semiconductor) or a piezoelectric material. The adhesive patch 406 can facilitate placement of the piezoelectric or piezoresistive sensor unit 306 in contact with the skin. The adhesive patch can include, for instance, a backing material such as a fabric or a flexible polymer, and an adhesive material capable of maintaining the placement of a sensor against the skin, including known dermal adhesives. The piezoelectric or piezoresistive sensor unit 306 send signals via the circuitry module 408 to an external device, such as a computer, tablet, or smart device (not shown in FIGS. 4A and 4B).

FIG. 4 depicts another exemplary system 500 according to one or embodiments of the invention. The system 500 includes a headband 504 including a piezoelectric or piezoresistive sensor unit 306 and a circuitry module 506. The headband 504 can be placed around a user's head 502 so as to position the sensor 306 near the temporal artery. The circuitry module 506, which can include communication circuitry, can be placed on the headband, as shown.

Figure 5B:
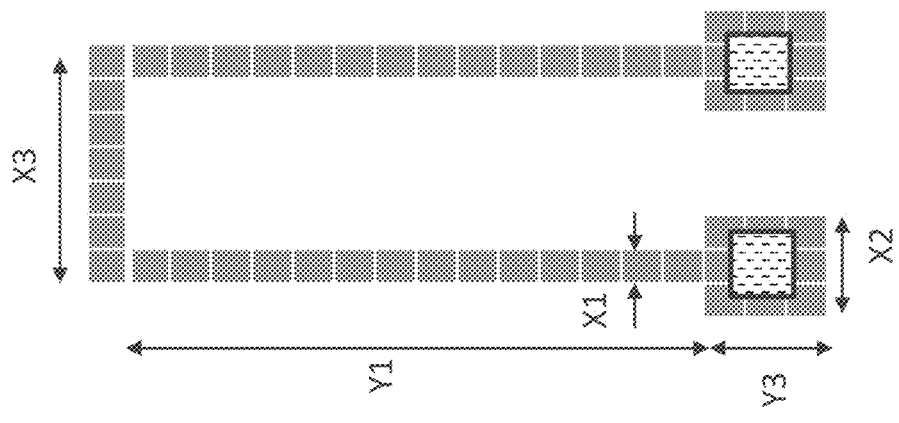
Figure 5A:
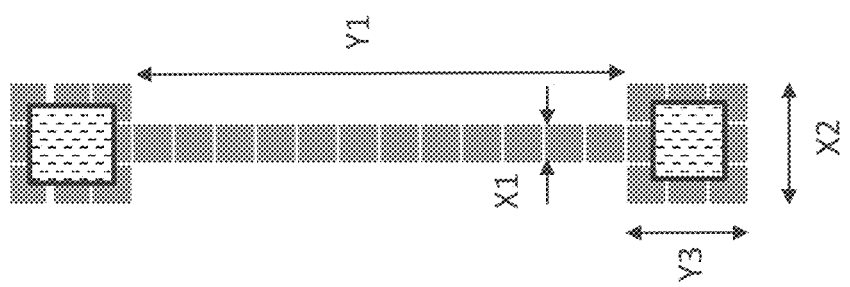
Figure 5D:
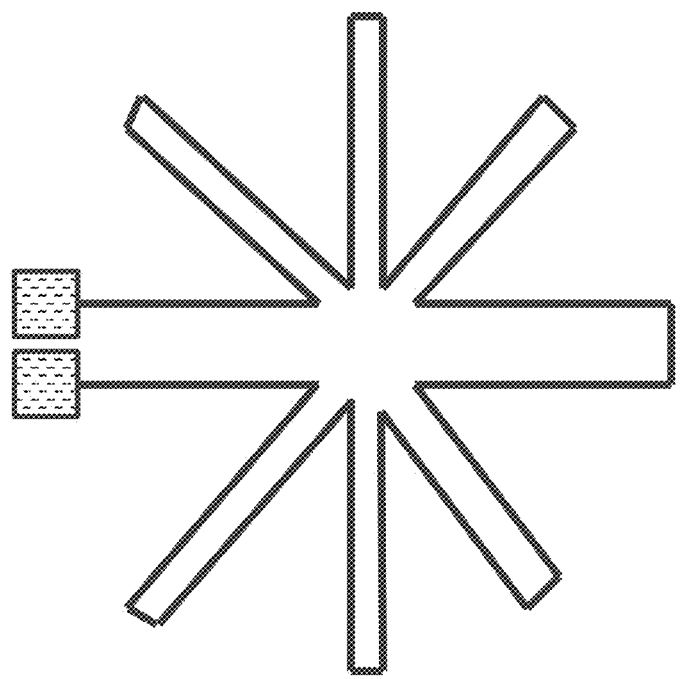
Figure 5C:
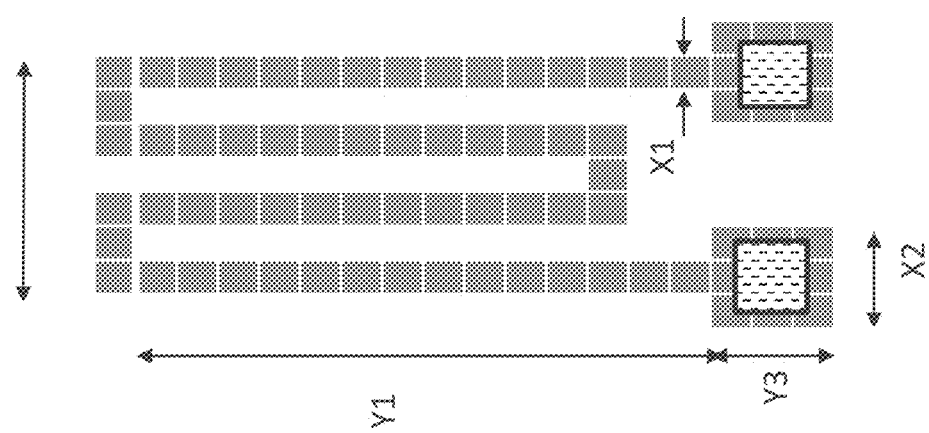
Figure 6:
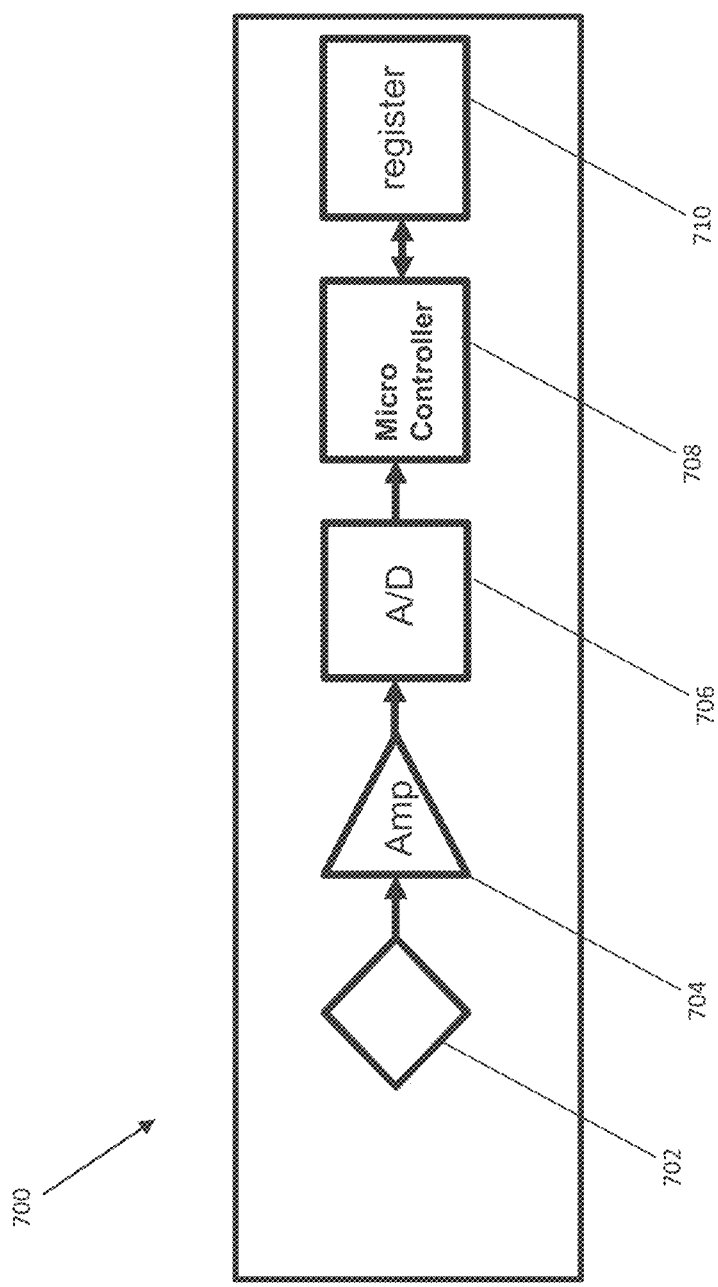
FIG. 6 depicts a schematic of aspects of an exemplary strain gauge sensor unit with piezoresistive-based strain gauge according to embodiments of the invention.
Figure 7:
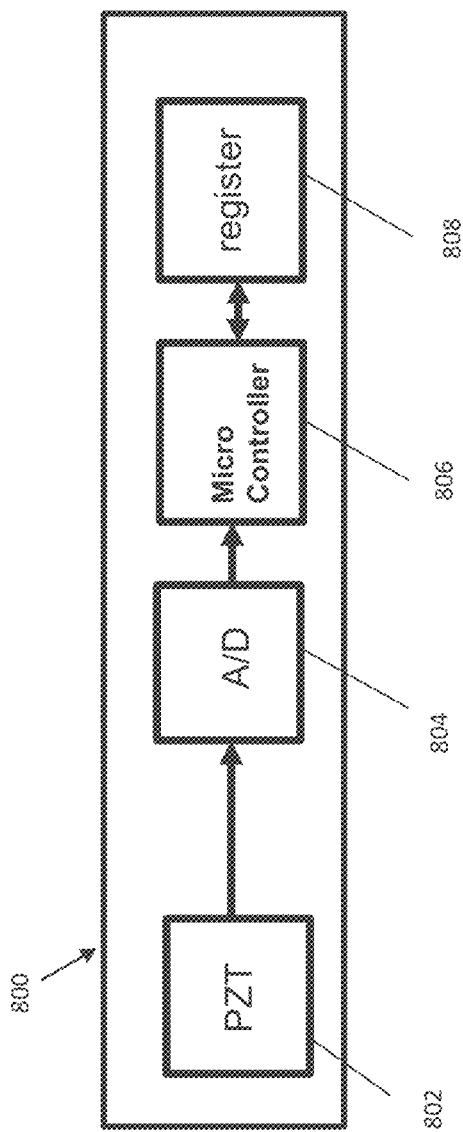
FIG. 7 depicts a schematic of aspects of an exemplary strain gauge sensor unit including a piezoelectric strain gauge according to embodiments of the invention.

Strain gauge sensor units according to embodiments of the invention, for instance systems as depicted in FIGS. 6 and 7, can be placed at single or multiple locations on a body. Embodiments of the invention including multiple strain gauge sensors can be formed in a variety of patterns and configurations. FIGS. 5A-5D depict shape of piezoresistive type strain gauge sensors according to embodiments of the invention.

FIG. 5A depicts a linear pattern in which two strain gauge sensing pads are in a linear configuration separated by a connecting line of distance Y1 from 50 µm to 50 mm, and having a width X1 from 2 µm to 10 mm. The sensing pads can each have a width X2 from 50 µm to 5 mm and height Y3 from 50 µm to 5 mm. FIG. 5B depicts a u-shaped pattern in which two sensing pads, in which the connecting line X3 can have a length, for instance of 6 µm to 30 mm. FIG. 5C and FIG. 5D depict alternate configurations including connecting lines including a plurality of deflection points.

FIG. 6 depicts a schematic of an exemplary strain gauge sensor unit 700 according to embodiments of the invention. The strain gauge sensor unit 700 includes a semiconductor-based strain gauge sensor including a Wheatstone bridge circuit 702. A Wheatstone bridge circuit 702 consists of resistors and it has the ability to provide accurate measurements. The unit 700 also includes an amplifier circuit 704 used for increasing amplitude of output signal from the Wheatstone bridge circuit 702 and an analog to digital (A/D) converter 706. The strain gauge sensor unit 700 can also include a microcontroller 708. The microcontroller 708 receives signals from A/D converter 706 and can have a capability of signal processing. In some embodiments of the invention, signal processing is performed by one or more external devices in communication with the exemplary strain gauge sensor unit 700. The strain gauge sensor unit 700 can also include a register 710 including, for instance, flash memory and/or SRAM.

FIG. 7 depicts a schematic of another exemplary strain gauge sensor unit 800 according to embodiments of the invention. The strain gauge sensor unit 800 includes a piezoelectric strain gauge sensor 802. The unit 800 also includes an analog to digital (A/D) converter 804 that converts the analog signals coming from the piezoelectric strain sensor 802 into digital signals for input into microcontroller 806. The strain gauge sensor unit 800 can also include a microcontroller 806. The microcontroller 806 receives signals from A/D Converter 804 and can have signal processing capabilities. The strain gauge sensor unit 800 can also include a register 808.

Advantageously, PZT sensors can be self-powered, for instance directly generating voltage that is a function of strain. In some embodiments of the invention, a piezoelectric strain gauge sensor unit does not have an external power system.

Figure 8:
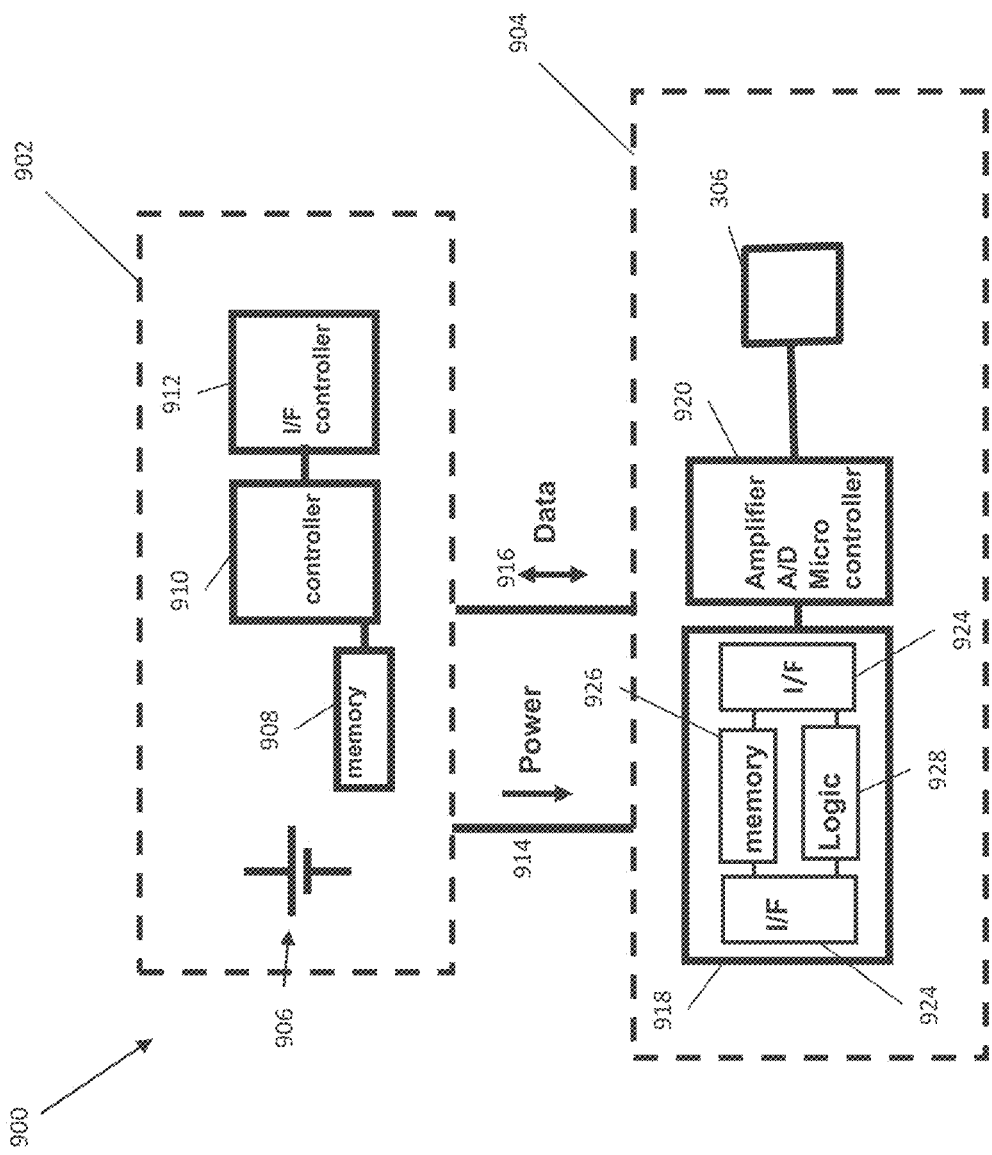
FIG. 8 depicts a schematic of aspects of an exemplary sensing system according to embodiments of the invention.

FIG. 8 depicts a schematic of an exemplary strain gauge sensor system 900 according to one or more embodiments of the invention. The system 900 includes a sensing patch or band 904 and an external computing device 902 electrically and mechanically connected by wires. The sensing patch or band 904 can include a strain gauge sensor integrated within an adhesive patch, wrist band, head band, leg band, or other patch or band suitable for positioning a strain gauge sensor at or near an artery.

The external computing device 902 can include a PC, tablet, smart phone or other portable device. The external computing device 902 includes, for instance, a power supply 906 such as a battery, memory 908, a controller 910, and an interface controller 912. The external computing device 902 can transfer power 914 and data 916 through wired connections to the sensing patch or band 904.

The sensing patch or band 904 can include an interface controller 918, a sensor control module 920, and a piezoelectric or piezoresistive sensor unit 306. The piezoelectric or piezoresistive sensor unit 306 can include a semiconductor based strain gauge sensor with a Wheatstone bridge circuit or a piezoelectric sensor. The interface controller 918 can include one or more interfaces 924 in communication with memory 926 and logic 928. The sensor control module 920 can include for instance an amplifier, an A/D converter and a microcontroller.

Figure 9:
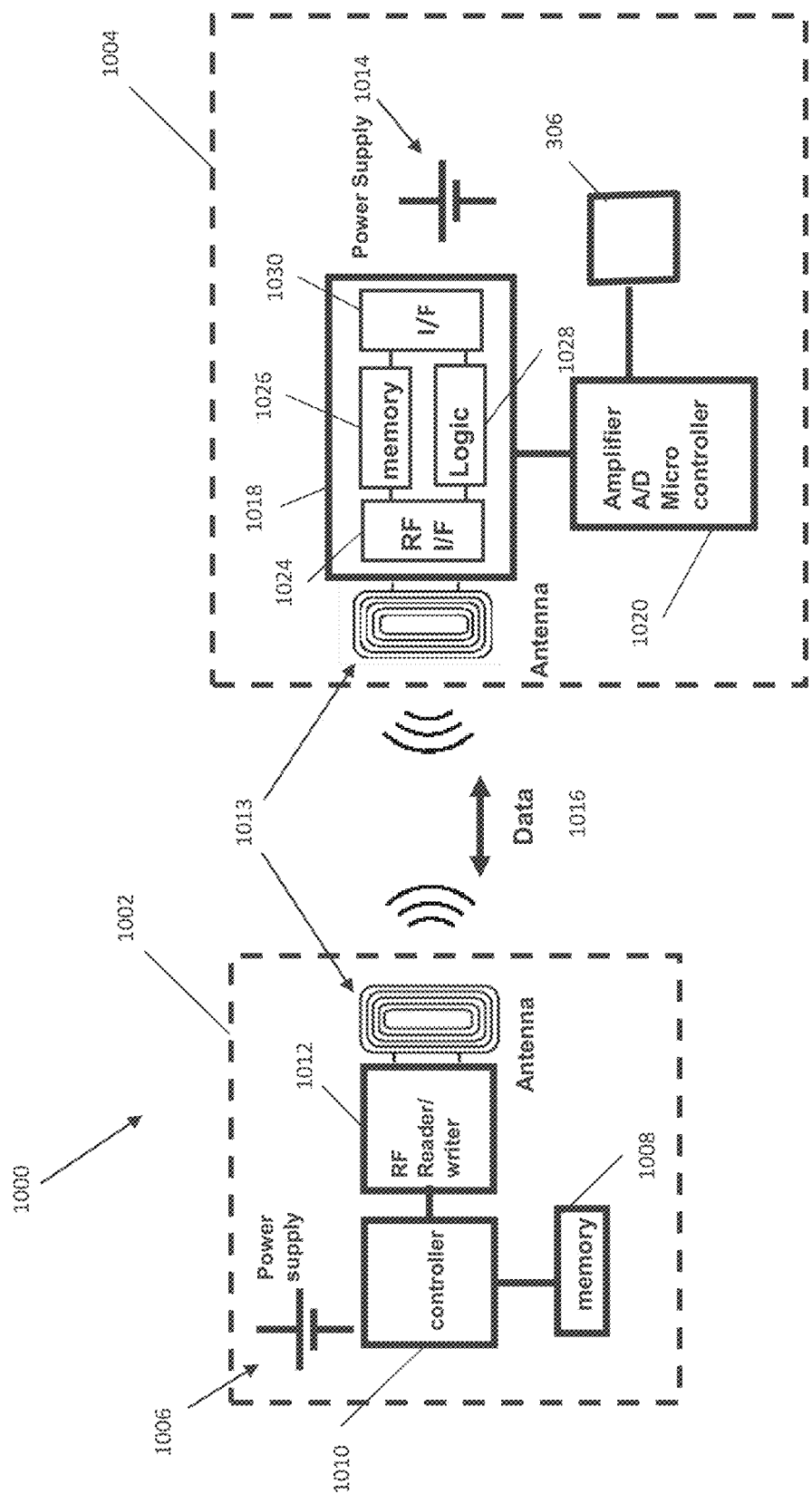
FIG. 9 depicts a schematic of aspects of another exemplary sensing system according to embodiments of the invention.

FIG. 9 depicts a schematic of another exemplary strain gauge sensor system 1000 according to one or more embodiments of the invention. The system 1000 includes a sensing unit 1004 and an external computing device 1002. The sensing patch or band can include a strain gauge sensor integrated within an adhesive patch, wrist band, head band, leg band, or other patch or band suitable for positioning a strain gauge sensor at or near an artery. In some embodiments, the sensing unit is a component of an implantable device, such as a device positioned at or near an artery. An implantable device includes a device that includes or has been treated with a biocompatible coating suitable for implantation within a subject.

The external computing device 1002 can include a PC, tablet, smart phone or other portable device. The external computing device 1002 includes, for instance, a power supply 1006 such as a battery, memory 1008, a controller 1010, and a radio frequency (RF) reader/writer 1012. The external computing device 1002 can send/receive data 1016 through a wireless connection (e.g. Bluetooth, WiFi, Near field communication (NFC), etc.) to the sensing unit 1004 by way of, for example, an electromagnetic field generated by antenna 1013 included in the external computing device 1002 and the sensing unit 1004. In some embodiments, not shown in FIG. 9, power can be transmitted to the sensing unit 1004 by NFC.

The sensing unit 1004 can include an RF interface controller 1018, a sensor control module 1020, a piezoelectric or piezoresistive sensor unit 306, and a power supply 1014. The piezoelectric or piezoresistive sensor unit 306 can include a semiconductor based strain gauge sensor with a Wheatstone bridge circuit or a piezoelectric sensor. In some embodiments of the invention, the system 1000 includes a piezoelectric strain gauge sensor in place of the semiconductor-based strain gauge sensor, without a Wheatstone bridge circuit. The interface controller 1018 can include an interface 1030 in communication with memory 1026, logic 1028, and RF interface 1024. The sensor control module 1020 can include for instance an amplifier, an analog to digital converter and a microcontroller.

In some embodiments of the invention, a strain gauge sensor is used in combination with other biosensors, such as heart rate monitors, pulse oximeters, thermometers, ECG instrumentation, respiration monitors, and the like. In some embodiments of the invention, systems include combinations of ECG sensors and strain gauge sensors.

Embodiments of the invention include methods for analyzing pressure pulse waves, heart rate variability, and/or arterial pressure derived from strain gauge sensors. Such methods can include obtaining a pressure pulse signal from a first strain gauge sensor, obtaining a pressure pulse signal from a second strain gauge sensor, wherein the second strain gauge sensor is positioned at a different location on a body than the first strain gauge sensor, and calculating the transit time of the blood from the first strain gauge sensor to the second strain gauge sensor. In some embodiments of the invention, a blood pressure is derived from the transit time. In some embodiments of the invention, a vascular stiffness parameter, such as an arterial stiffness index or other arterial stiffness characteristic, is derived from the transit time. In some embodiments of the invention, methods include extracting information from the pressure pulse signal waveform, for instance by machine learning. For example, the pressure pulse signal can be obtained over a period of time or over multiple periods of time for a subject and/or for other subjects and saved in a pressure pulse signal database. A pressure pulse signal can be compared to the pressure pulse signal database and unique, abnormal, or infrequent signal features and/or signal features associated with or that correlate to abnormal or problematic conditions can be derived from the pressure pulse signal based upon the database.

In some embodiments of the invention, strain gauge sensors are used for continuous determination of systolic and diastolic arterial pressure.

Embodiments of the invention include detection of heart failure by obtaining a pressure pulse signal from a strain gauge sensor and determining the presence or absence of heart failure by analyzing the pressure pulse signal.

Figure 10:
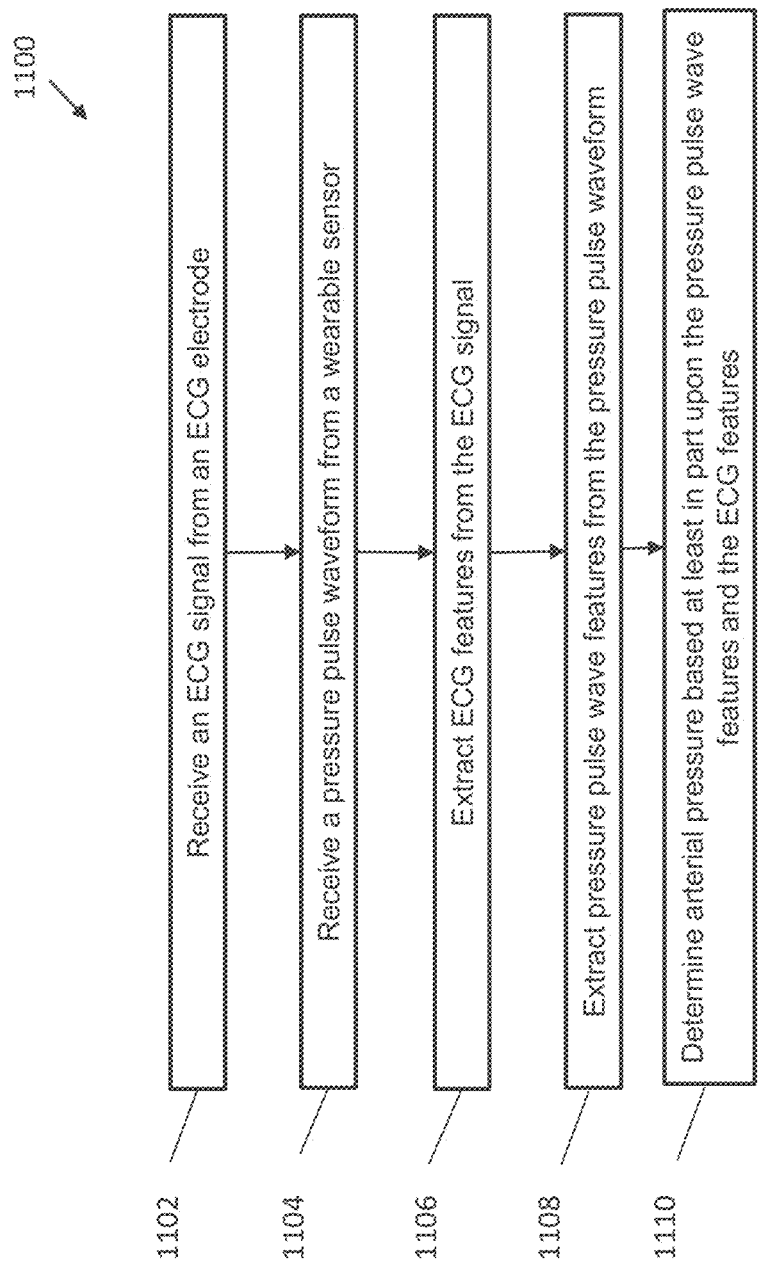
FIG. 10 depicts a flow diagram of an exemplary method according to embodiments of the invention.

FIG. 10 depicts a flow diagram of a method 1100 for determining arterial pressure according to one or more embodiments of the present invention. The method 1100 includes, as shown at block 1102 receiving an ECG signal from an ECG electrode.

The method 1100 includes, as shown at block 1104 receiving a pressure pulse waveform from a wearable sensor, such as a sensor including a piezoelectric or piezoresistive material, such as a strain gauge sensor. The pressure pulse waveform can be recorded by plethysmography using a single semiconductor strain gauge sensing unit, such as a patch, band, or implantable device or a strain gauge sensing unit in combination with other biosensors, such as light sensors or other devices for plethysmography.

In some embodiments of the invention, ECG and/or plethysmography signals can be filtered with standard signal processing routines. In some embodiments of the invention, signal processing is performed by a device external to a wearable or implantable device. The method 1100 includes, as shown at block 1106, extracting features from the ECG signal, such as an R-peak of a QRS complex and RR-intervals between neighboring QRS waves. The method 1100 includes, as shown at block 1108, extracting pressure pulse wave features from the pressure pulse waveform, such as time of onset of the pulse pressure wave, time of wave peak, and time of the peak of reflection wave.

The method 1100 includes, as shown at block 1110, determining arterial pressure based at least in part upon the pressure pulse wave features and the ECG features. For instance, systolic and diastolic arterial pressure can be estimated or determined based at least in part upon the interval between the R-peak and the onset of the blood pressure wave RP1 (as depicted in FIG. 1), the interval between the onset of the pressure wave and the peak P1P2 (as depicted in FIG. 1) of point P1 206 and point P2 208, and the RR-intervals (RR, as depicted in FIG. 1). Arterial pressure or blood pressure can be computed based on linear regression or non-linear formulas derived from wave propagation principles.

Figure 11:
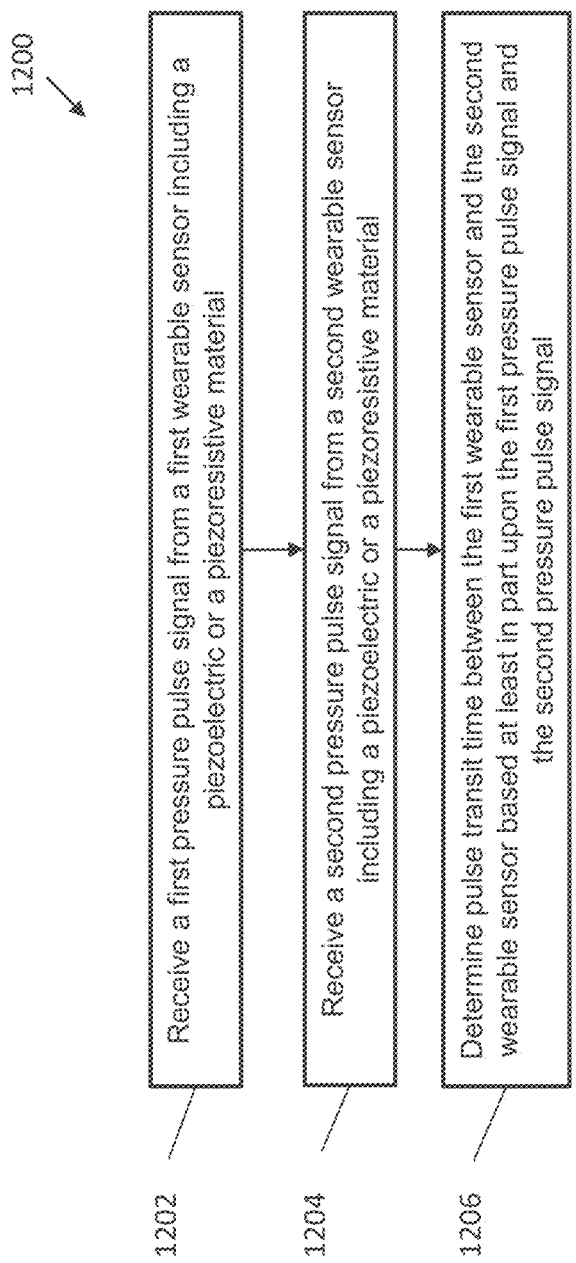
FIG. 11 depicts a flow diagram of another exemplary method according to embodiments of the invention.

FIG. 11 depicts a flow diagram of another method 1200 for determining arterial pressure according to one or more embodiments of the present invention. The method 1200 includes, as shown at block 1202, receiving a first pressure pulse signal from a first wearable sensor including a piezoelectric or piezoresistive material. The method 1200 includes, as shown at block 1204, receiving a second pressure pulse signal from a second wearable sensor including a piezoelectric or piezoresistive material. For instance, a strain gauge sensor can be placed near a carotid artery and another strain gauge sensor can be placed on the wrist. The method 1200 includes, as shown at block 1206, determining a pulse transit time between the first strain gauge sensor and the second strain gauge sensor based at least in part upon the first pressure pulse signal and the second pressure pulse signal.

In some embodiments of the invention, a pressure pulse signal is processed by an external device, such as a computer, tablet, or smart device in communication with the sensor, for example via circuitry in proximity to the sensor.

In some embodiments of the invention, a pressure pulse signal is analyzed in the cloud.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Figure 12:
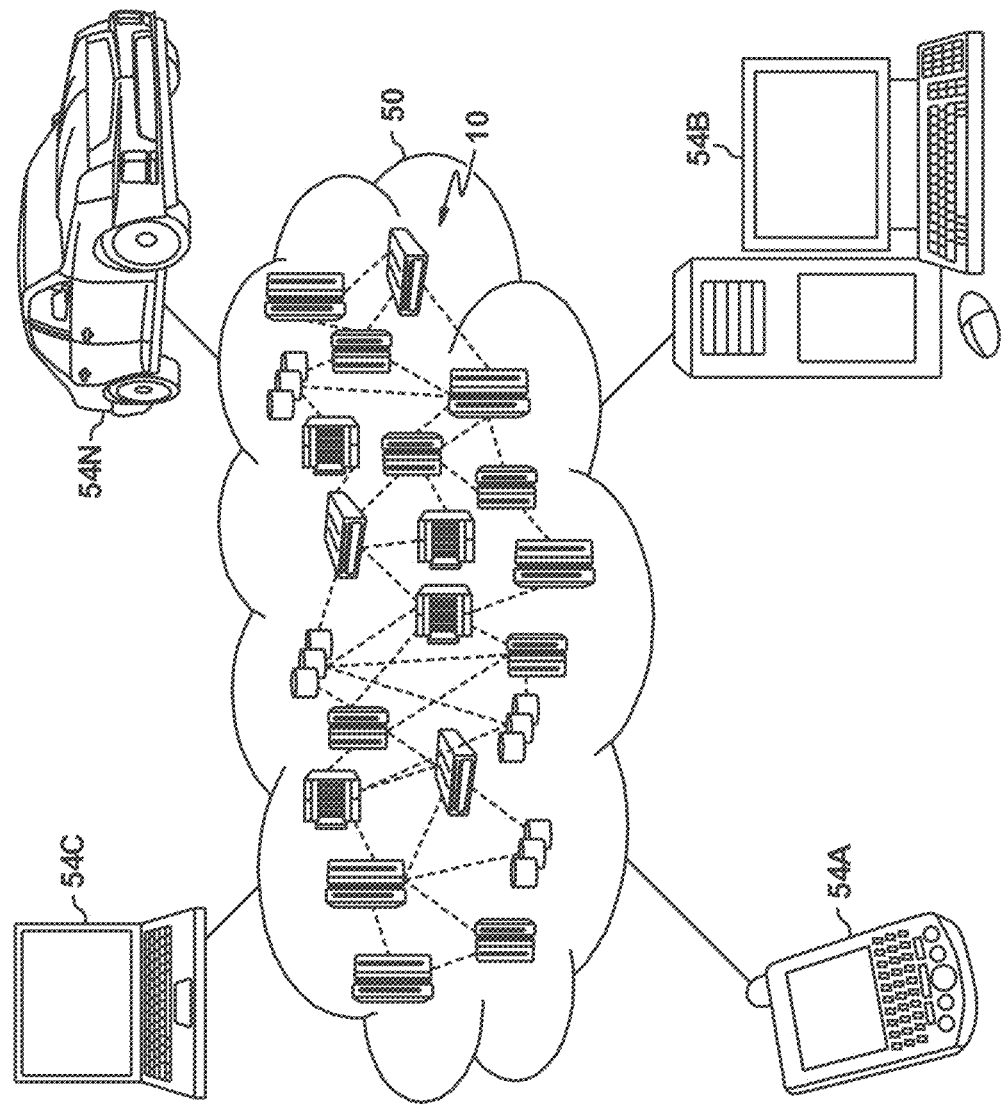
FIG. 12 depicts a cloud computing environment according to an embodiment of the present invention.

Referring now to FIG. 12, illustrative cloud computing environment 50 according to one or more embodiments of the present invention is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 12 are intended to be illustrative only and that computing nodes 10 and cloud computing environment 50 can communicate with any type of computerized device over any type of network and/or network addressable connection (e.g., using a web browser).

Figure 13:
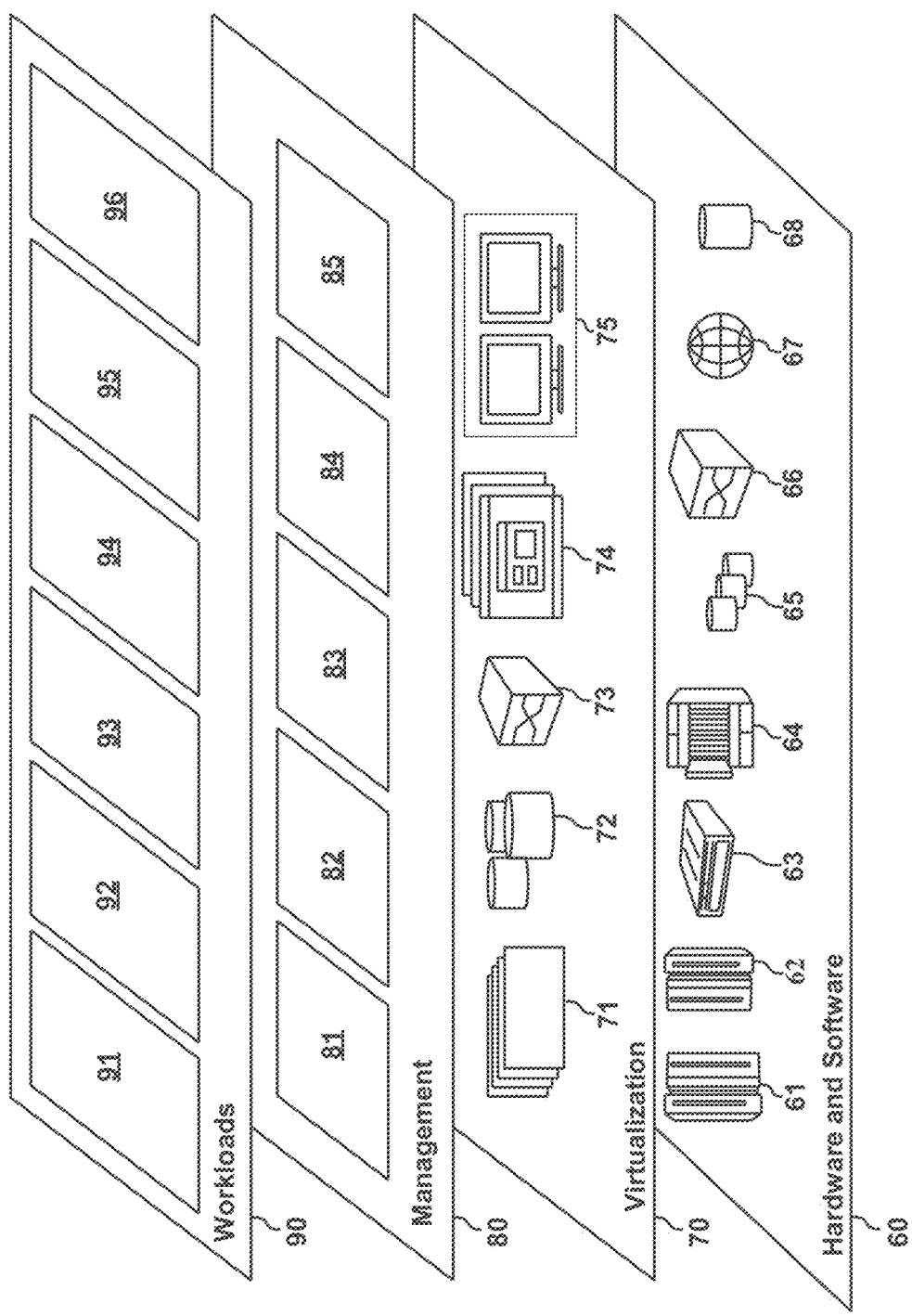
FIG. 13 depicts abstraction model layers according to an embodiment of the present invention.

Referring now to FIG. 13, a set of functional abstraction layers provided by cloud computing environment 50 (FIG. 12) according to one or more embodiments of the present invention is shown. It should be understood in advance that the components, layers, and functions shown in FIG. 13 are intended to be illustrative only and embodiments of the invention are not limited thereto. As depicted, the following layers and corresponding functions are provided:

Hardware and software layer 60 includes hardware and software components. Examples of hardware components include: mainframes 61; RISC(Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and determining arterial pressure 96.

Figure 14:
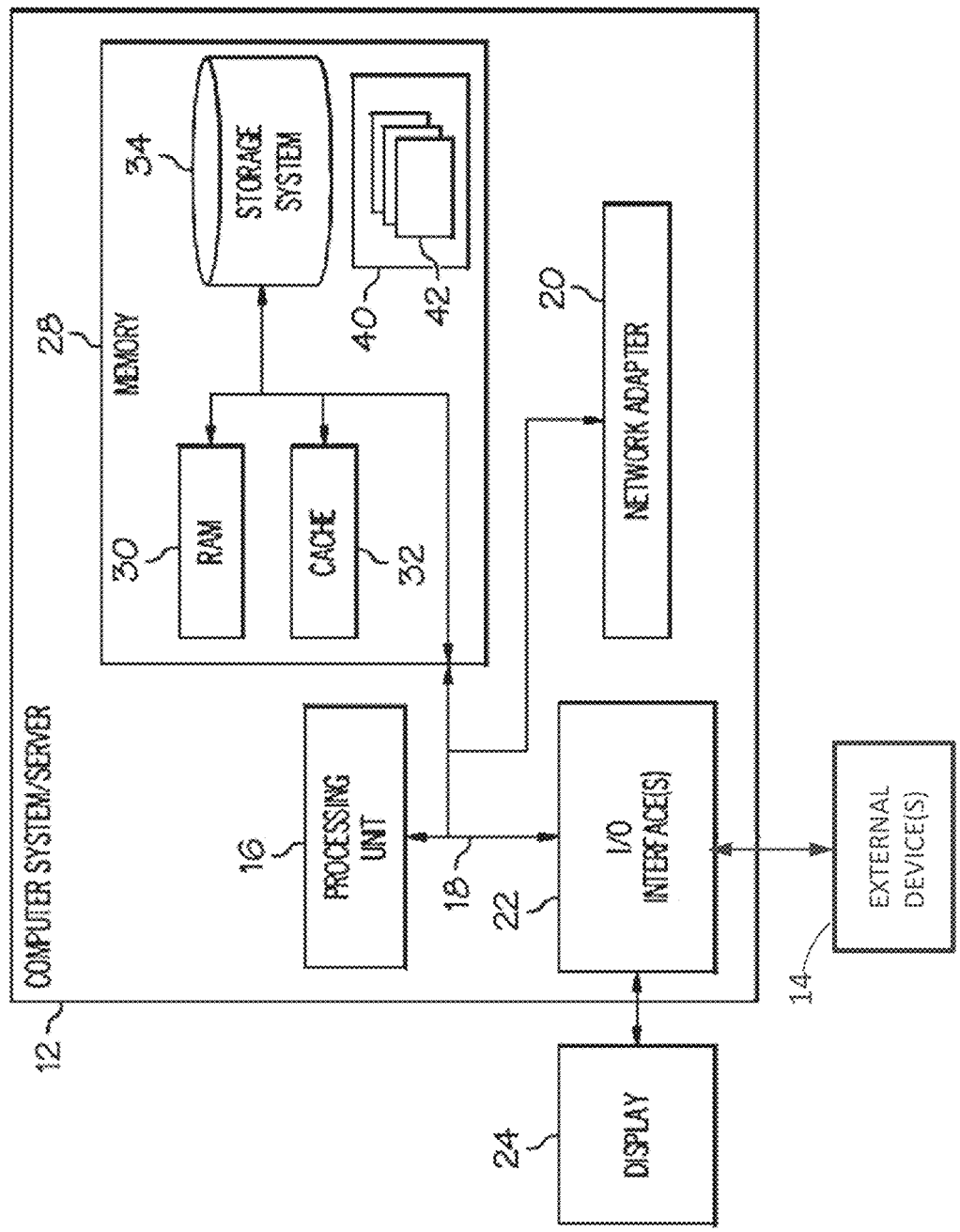
FIG. 14 depicts a computer system according to one or more embodiments of the present invention.

Referring now to FIG. 14, a schematic of a cloud computing node 100 included in a distributed cloud environment or cloud service network is shown according to one or more embodiments of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 14, computer system/server 12 in cloud computing node 100 is shown in the form of a general-purpose computing device. The components of computer system/server 12 can include, but are not limited to, one or more processors or processor 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 15:
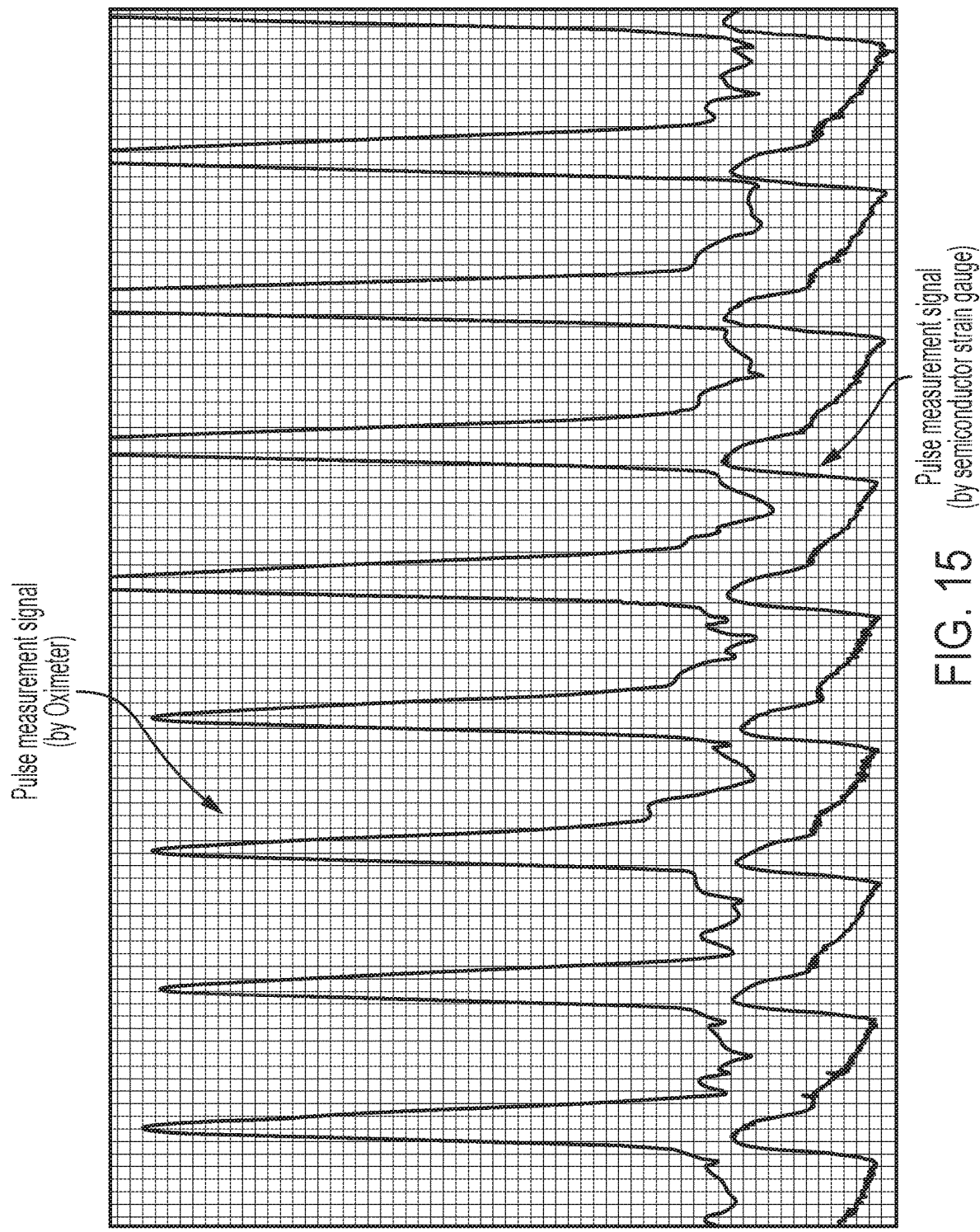
FIG. 15 depicts data obtained with an exemplary system according to embodiments of the invention as well as data obtained with a conventional oximetric system for comparison.

Example 1—Comparison Between Strain Gauge Sensor and Conventional Pulse Oximeter A semiconductor-based strain gauge sensor according to embodiments of the invention was applied to a wrist of a human subject with an adhesive material and connected to an external computing unit via a wired communication. A pulse measurement signal was obtained by the semiconductor-based strain gauge sensor and compared to a pulse measurement signal collected by a conventional pulse oximeter. The pulse measurement signals obtained are depicted in FIG. 15. As is shown, the strain gauge sensor correctly detects the periodicity of the pulse pressure signal, similar to prior art systems such as the pulse oximeter.

Example 2—Embodiment Including ECG and Strain Gauge Sensors

Figure 16B:
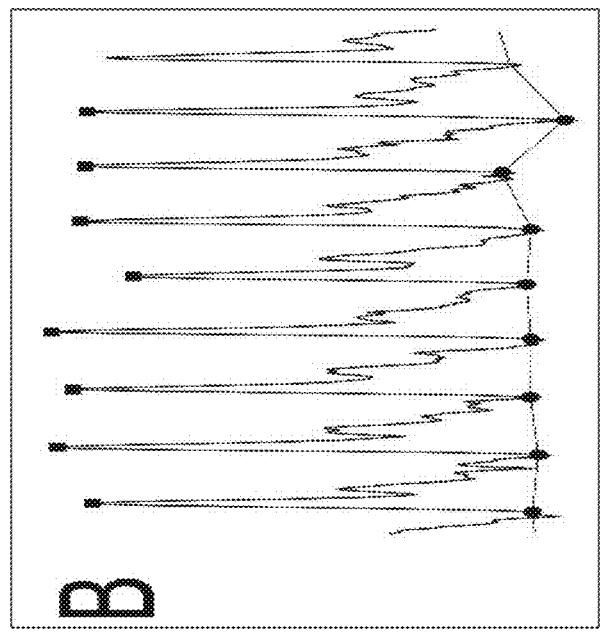
Figure 16A:
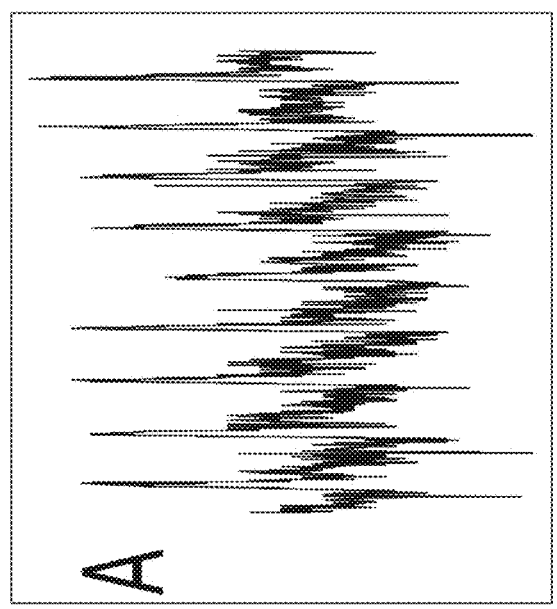
Figure 16C:
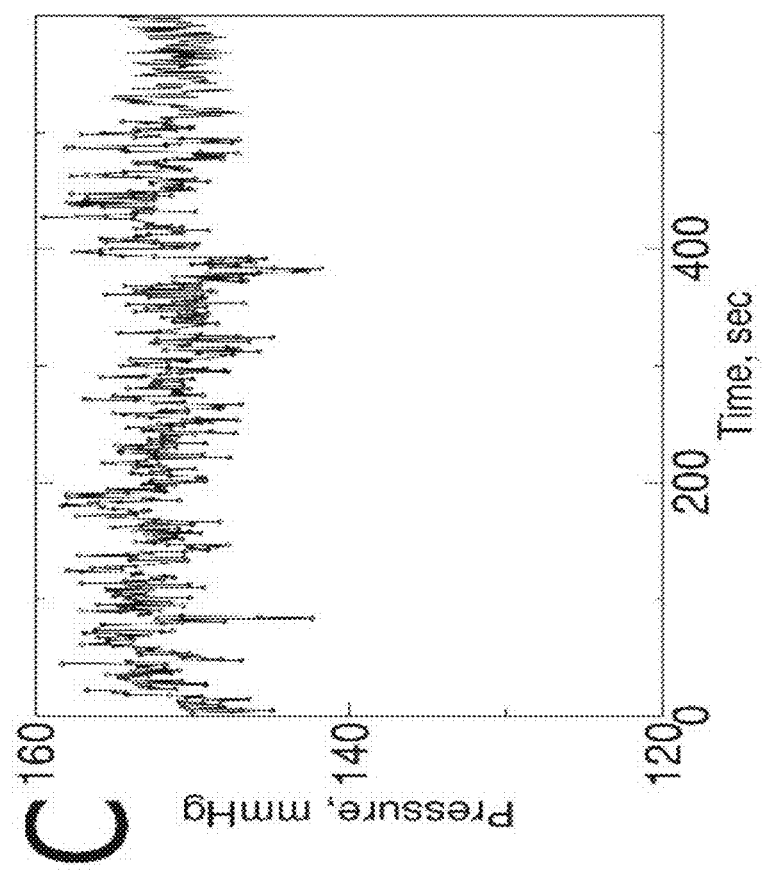

An ECG and a signal from a strain gauge sensor were simultaneously obtained for a subject known to have high systolic blood pressure. A strain gauge sensor recording was obtained for a period of ten minutes. FIG. 16A shows the pressure pulse wave form obtained from the strain gauge sensor. FIG. 16B depicts the data obtained from the strain gauge sensor after filtering and extraction of features for estimation of blood pressure. After initial calibration with a conventional arm pressure cuff system, Systolic blood pressure was calculated from the filtered and extracted data by the Moens-Korteweg equation. Estimated pressure tracing is shown in FIG. 16C. A second arm cuff pressure measurement was performed at the end of the ten-minute session, showing good agreement between the conventional pressure cuff system and the combined ECG-strain gauge system.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments of the invention, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments of the invention, the practical application or technical improvement over technologies found in the marketplace, or to enable others of ordinary skill in the art to understand the embodiments described herein.

What is claimed is:

1. A computer-implemented method for operating a biological monitoring system, comprising:
receiving, by a processor of-in the biological monitoring system on a wrist of a subject in which the biological monitoring system is at a location on the subject, a first pressure pulse signal from a first semiconductor strain gauge sensor of the biological monitoring system at the location, wherein the first semiconductor strain gauge is doped using a doping material, the biological monitoring system being a self-contained portable unit comprising the processor, the first semiconductor strain gauge sensor, and a register, the register being configured to record the first pressure pulse signal, the biological monitoring system having a protrusion pressed against the wrist of the subject, wherein the first semiconductor strain gauge sensor comprises a piezoresistive material or a piezoelectric material, wherein the biological monitoring system comprises a band, the protrusion being formed on the band, wherein the piezoresitive material or the piezoelectric material is arranged along an entire contour of the protrusion and configured to be positioned against the subject's skin;
receiving, by the processor, a second pressure pulse signal from a second semiconductor strain gauge sensor, the register being configured to record the second pressure pulse signal wherein the second semiconductor strain gauge is doped using the doping material;
calculating, by the processor of the biological monitoring system at the location, a pulse transit time between the first semiconductor strain gauge sensor and the second semiconductor strain gauge sensor based at least in part upon the first pressure pulse signal and the second pressure pulse signal;
providing, using a Moens-Korteweg equation by the processor of the biological monitoring system at the location, an arterial pressure of the subject based at least in part upon the pulse transit time; and
storing, by the processor of the biological monitoring system, the first and second pressure pulse signals in a pulse pressure signal database for the subject over a period of time, thereby enabling the subject to manage cardiovascular disease and heart rate variability.

2. The computer-implemented method of claim 1, wherein the first pressure pulse signal or the second pressure pulse signal is communicated wirelessly to the processor.

3. The computer-implemented method of claim 1, wherein the second pressure pulse signal comprises a carotid artery signal, and the first pressure pulse signal comprises a radial artery signal.

4. The computer-implemented method of claim 1, further comprising analyzing the first pressure pulse signal or the second pressure pulse signal in a cloud-based environment.

5. The computer-implemented method of claim 1, wherein the first semiconductor strain gauge sensor and the second semiconductor strain gauge sensor are in electrocardiogram (ECG) electrodes that are used to record an ECG.

6. The computer-implemented method of claim 1, wherein the protrusion is formed of a same material as the band.

\* \* \* \* \*